(12) United States Patent
King et al.

(10) Patent No.: US 10,454,035 B2
(45) Date of Patent: Oct. 22, 2019

(54) ORGANIC SEMICONDUCTORS WITH DITHIENOFURAN CORE MONOMERS

(71) Applicant: International Business Machines Corporation, Armonk, NY (US)

(72) Inventors: Scott B. King, Rochester, MN (US); Brandon M. Kobilka, Tucson, AZ (US); Joseph Kuczynski, North Port, FL (US); Jason T. Wertz, Pleasant Valley, NY (US)

(73) Assignee: International Business Machines Corporation, Armonk, NY (US)

( * ) Notice: Subject to any disclaimer, the term of this patent is extended or adjusted under 35 U.S.C. 154(b) by 0 days.

(21) Appl. No.: 16/381,865

(22) Filed: Apr. 11, 2019

(65) Prior Publication Data

US 2019/0245145 A1 Aug. 8, 2019

Related U.S. Application Data

(62) Division of application No. 15/287,713, filed on Oct. 6, 2016, now Pat. No. 10,312,444.

(51) Int. Cl.
*H01L 51/00* (2006.01)
*C07D 495/14* (2006.01)
(Continued)

(52) U.S. Cl.
CPC ........ *H01L 51/0036* (2013.01); *C07D 307/68* (2013.01); *C07D 495/14* (2013.01);
(Continued)

(58) Field of Classification Search
CPC ............. H01L 51/0036; H01L 51/0043; H01L 51/0071; C07D 307/68; C07D 495/14;
(Continued)

(56) References Cited

U.S. PATENT DOCUMENTS 9,093,601 B2 7/2015 Yamazaki et al.
9,299,937 B2 3/2016 Lee et al.
(Continued)

FOREIGN PATENT DOCUMENTS

CN 103984817 A 8/2014
CN 105405976 A 3/2016
(Continued)

OTHER PUBLICATIONS

Guo et al., "Dithiafulvenyl Unit as a New Donor for High-Efficiency Dye-Sensitized Solar Cells: Synthesis and Demonstration of a Family of Metal-Free Organic Sensitizers," Organic Letters, 2012, vol. 14, No. 9, pp. 2214-2217, © 2012 American Chemical Society.
(Continued)

*Primary Examiner* — Seahvosh Nikmanesh
(74) *Attorney, Agent, or Firm* — Kelsey M. Skodje

(57) ABSTRACT

An organic semiconducting donor-acceptor (D-A) small molecule, as well as a semiconductor device that can incorporate the D-A small molecule, are disclosed. The D-A small molecule can have electron deficient substituents and R group substituents that can be $C_1$-$C_{20}$ linear alkyl chains, $C_2$-$C_{24}$ branched alkyl chains, hydrogen atoms, etc. The D-A small molecule can be can be synthesized in a reaction between a dithienofuran (DTF) core monomer and an electron deficient monomer. Additionally, the D-A small molecule can be part of an organic semiconducting copolymer. A semiconductor device that can incorporate the D-A small molecule in a photoactive layer is also disclosed herein. Additionally, 3,4-dibrominated furan compound that can, in some embodiments, be a precursor for the D-A small molecule is disclosed. The 3,4-dibrominated furan compound can be synthesized in a reaction involving a furan-2,5-dicarboxylic dimethyl ester (FDME), which can have a bio-renewable precursor.

10 Claims, 14 Drawing Sheets

(51) Int. Cl.
*C08G 61/12* (2006.01)
*C07D 307/68* (2006.01)
*H01L 51/05* (2006.01)
*H01L 51/42* (2006.01)

(52) U.S. Cl.
CPC ......... *C08G 61/122* (2013.01); *C08G 61/125* (2013.01); *C08G 61/126* (2013.01); *H01L 51/0043* (2013.01); *H01L 51/0071* (2013.01); *C08G 2261/228* (2013.01); *C08G 2261/3222* (2013.01); *C08G 2261/3241* (2013.01); *C08G 2261/3242* (2013.01); *C08G 2261/3243* (2013.01); *C08G 2261/3246* (2013.01); *C08G 2261/3247* (2013.01); *C08G 2261/334* (2013.01); *C08G 2261/411* (2013.01); *C08G 2261/414* (2013.01); *C08G 2261/91* (2013.01); *C08G 2261/92* (2013.01); *C08G 2261/94* (2013.01); *H01L 51/0558* (2013.01); *H01L 51/42* (2013.01); *H01L 51/4253* (2013.01); *Y02E 10/549* (2013.01)

(58) Field of Classification Search
CPC ... C08G 61/122; C08G 61/125; C08G 61/126
See application file for complete search history.

(56) References Cited

U.S. PATENT DOCUMENTS

| | | | |
|---|---|---|---|
| 10,062,847 B2* | 8/2018 | King | ............ H01L 51/0036 |
| 2009/0203873 A1* | 8/2009 | Sotzing | ............ C08G 61/126 528/380 |
| 2012/0097935 A1 | 4/2012 | Kimer et al. | |
| 2014/0167002 A1 | 6/2014 | Welch et al. | |
| 2014/0290748 A1 | 10/2014 | Demadrille et al. | |
| 2015/0132887 A1 | 5/2015 | Welker et al. | |
| 2015/0136224 A1 | 5/2015 | Shi et al. | |

FOREIGN PATENT DOCUMENTS

| | | |
|---|---|---|
| CN | 105585693 A | 5/2016 |
| JP | 2014139982 A | 7/2014 |
| WO | 2010037068 A2 | 4/2010 |

OTHER PUBLICATIONS

Lee et al., "Dye-Sensitized Solar Cells Based on (Donor-π-Acceptor)2 Dyes With Dithiafulvalene as the Donor," Chemistry, An Asian Journal, 2014, 9, pp. 1933-1942, © 2014 Wiley-VCH Verlag GmbH & Co. KGaA, Weinheim.

Kozmik et al., "Dithieno[3,2-b:2',3'-d]furan as a new building block for fused conjugated systems," Tetrahedron Letters, vol. 56, Issue 45, Nov. 4, 2015, pp. 6251-6253.

Kwon et al., "Dithienothiophene (DTT)-Based Dyes for Dye-Sensitized Solar Cells: Synthesis of 2,6-Dibromo-DTT," JOC| The Journal of Organic Chemistry, 2011, 76(10), pp. 4088-4093, Copyright © 2011 American Chemical Society.

SciFinder Structure search of all DTF functionalized heterocycles, SciFinder®, printed Feb. 26, 2016, 8 pages, Copyright © 2016 American Chemical Society (ACS).

Zhang et al., "Heteroatom Substitution of Oligothienoacenes: From Good p-Type Semiconductors to Good Ambipolar Semiconductors for Organic Field-Effect Transistors," The Journal of Physical Chemistry, 2008, 112(13), pp. 5148-5159, Copyright © 2011 American Chemical Society.

Cheng et al., "Synthesis of Conjugated Polymers for Organic Solar Cell Applications," Chemical Reviews, 2009, 109, pp. 5868-5923, published Sep. 29, 2009, © 2009 American Chemical Society.

"2,2,6,6-Tetramethylpiperidinylmagnesium chloride lithium chloride complex solution," Sigma-Aldrich, CAS No. 898838-07-8, printed Jun. 3, 2016, 1 page, http://www.sigmaaldrich.com/catalog/search?term=898838-07-8&interface=CAS%20No.&N=0&mode=match%20partialmax&lang=en&region=US&focus=product.

"DuPont Industrial Biosciences and ADM Announce Breakthrough Platform Technology for Long Sought-After Molecule," Press Release, Jan. 19, 2016, 3 pages, http://www.dupont.com/products-and-services/industrial-biotechnology/press-releases/dupont-adm-announce-platform-technology-for-long-sought-after-molecule.html.

King et al., "Organic Semiconductors with Dithienofuran Core Monomers," U.S. Appl. No. 15/287,713, filed Oct. 6, 2016.

King et al., "Organic Semiconductors with Dithienofuran Core Monomers," U.S. Appl. No. 15/857,763, filed Dec. 29, 2017.

List of IBM Patents or Patent Applications Treated as Related, Signed Apr. 11, 2019, 2 pages.

* cited by examiner

FRUCTOSE
305

D-GLUCARIC ACID
310

FDME
110

FDCA
315

DTF CORE MONOMER
710

| Z = | Br | 140 |
| --- | --- | --- |
| Z = | (pinacol boronate) | 510 |
| Z = | —Sn(CH₃)₃ | 610 |

ORGANIC SEMICONDUCTORS WITH DITHIENOFURAN CORE MONOMERS

BACKGROUND

The present disclosure relates to semiconducting organic materials and, more specifically, electron donor-acceptor copolymers and small molecules with substituted dithienofuran core monomers.

Organic semiconducting polymers and small molecules have many applications in electronic devices. Organic semiconductors differ from inorganic semiconductors, such as silicon, in a number of ways. One way is that organic semiconductors can be less expensive than inorganic semiconductors. Organic semiconductors can also be flexible, allowing them to be incorporated into a wide variety of materials and technologies. Some organic semiconductors can be used in optoelectronic devices, such as solar cells or light sensors. Organic semiconductors known as organic photovoltaic (OPV) materials, can produce an electrical current upon exposure to photons. Organic semiconductors can be produced from non-renewable petroleum-based resources or bio-renewable sources.

SUMMARY

Various embodiments are directed to organic semiconducting donor-acceptor (D-A) small molecules and semiconductor devices that can incorporate the organic semiconducting D-A molecules. The D-A small molecules can be substituted dithienofuran (DTF) core monomers bound to electron deficient monomers. Substituents on the DTF core monomer can be R groups such as $C_1$-$C_{20}$ linear alkyl chains, a $C_2$-$C_{24}$ branched alkyl chains, etc. In some embodiments, a 3,4-dibrominated furan compound can be a precursor of the DTF core monomers. The 3,4-dibrominated furan compound can be synthesized in a reaction involving furan-2,5-dicarboxylic dimethyl ester (FDME), which can have a bio-renewable precursor. Examples of bio-renewable precursors can include sugars and aldaric acids.

The D-A small molecule can be synthesized in a reaction between a DTF core monomer and an electron deficient monomer. Examples of electron deficient monomers that can be bound to the DTF core, providing the D-A small molecule with electron deficient substituents, can include bromoalkylthienyl-pyridylthiazoles, benzodithiazoles, pyridyldithiazoles, diketopyrrolopyrroles, thienopyrrolodiones, thienothiophene esters, fluorinated thienothiophene esters, dithienotetrazines, thienoquinoxalines, benzoquinoxalines, pyridylquinoxalines, etc. The D-A small molecule can also be part of an organic semiconducting copolymer with repeating units of the DTF core monomer and electron deficient monomer.

The organic semiconducting D-A small molecules and copolymers can be in the semiconducting, photoactive layers of semiconductor devices. These devices can include a first and a second electrode, which can comprise at least one conductive material, such as a metal, a metal oxide, a metal alloy, a conductive polymer, Ag nanowires, Cu nanowires, graphene, carbon nanotubes, a polymer-metal hybrid, carbon-sulfur nanotubes, nanofibers, an organic polymer, etc. The semiconducting layer can be a bilayer or a bulk heterojunction, and it can include materials in addition to the D-A small molecules or copolymers, such as fullerenes, polymers, and polymer blends. Examples of semiconductor devices that can incorporate the organic semiconducting compounds can include organic photovoltaic cells (OPVs), field effect transistors (FETs), light sensors, etc.

DETAILED DESCRIPTION

Figure 1A:
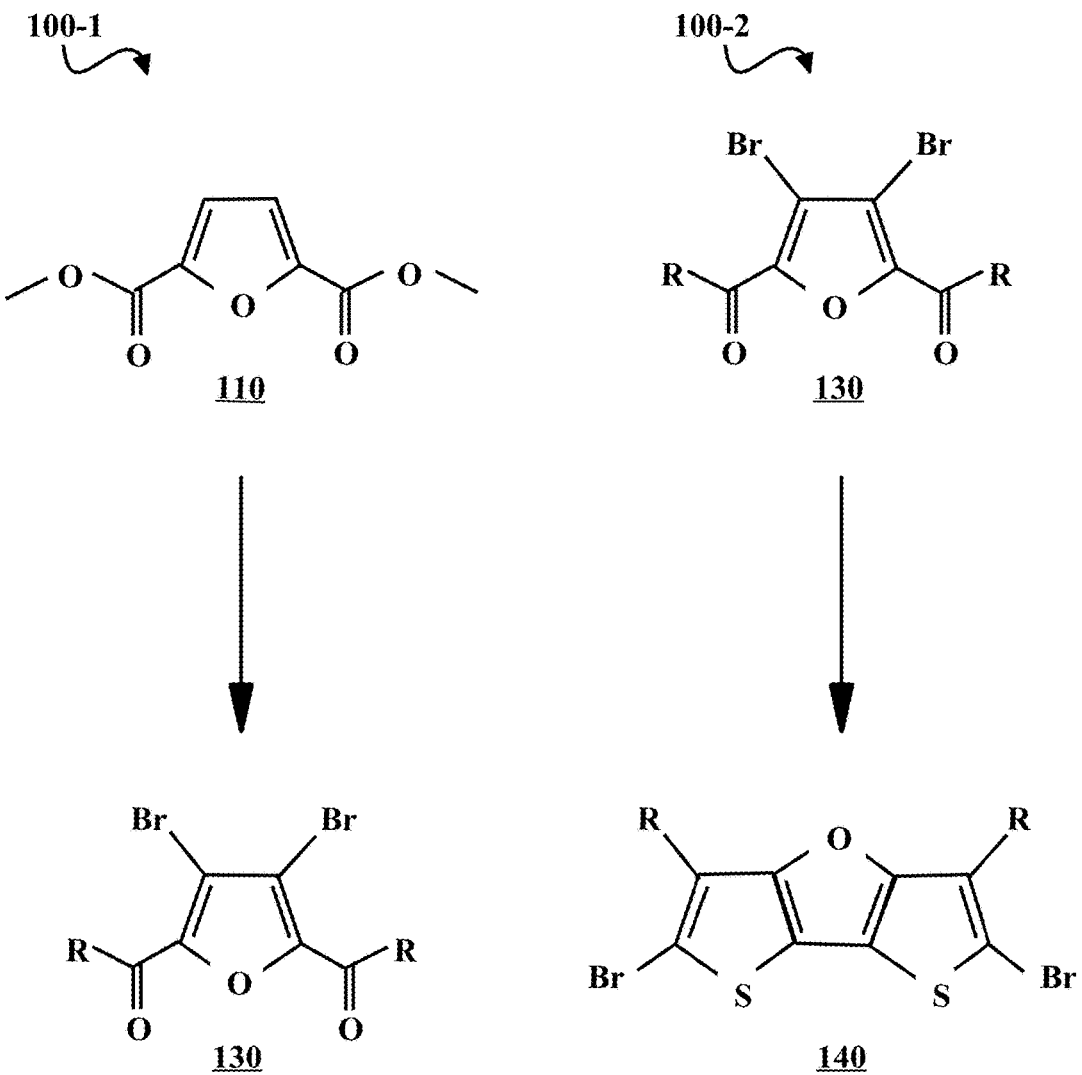
FIG. 1A is a diagrammatic summary of steps in processes of forming a dibrominated furan compound and a dithienofuran compound, according to some embodiments.
Figure 1B:
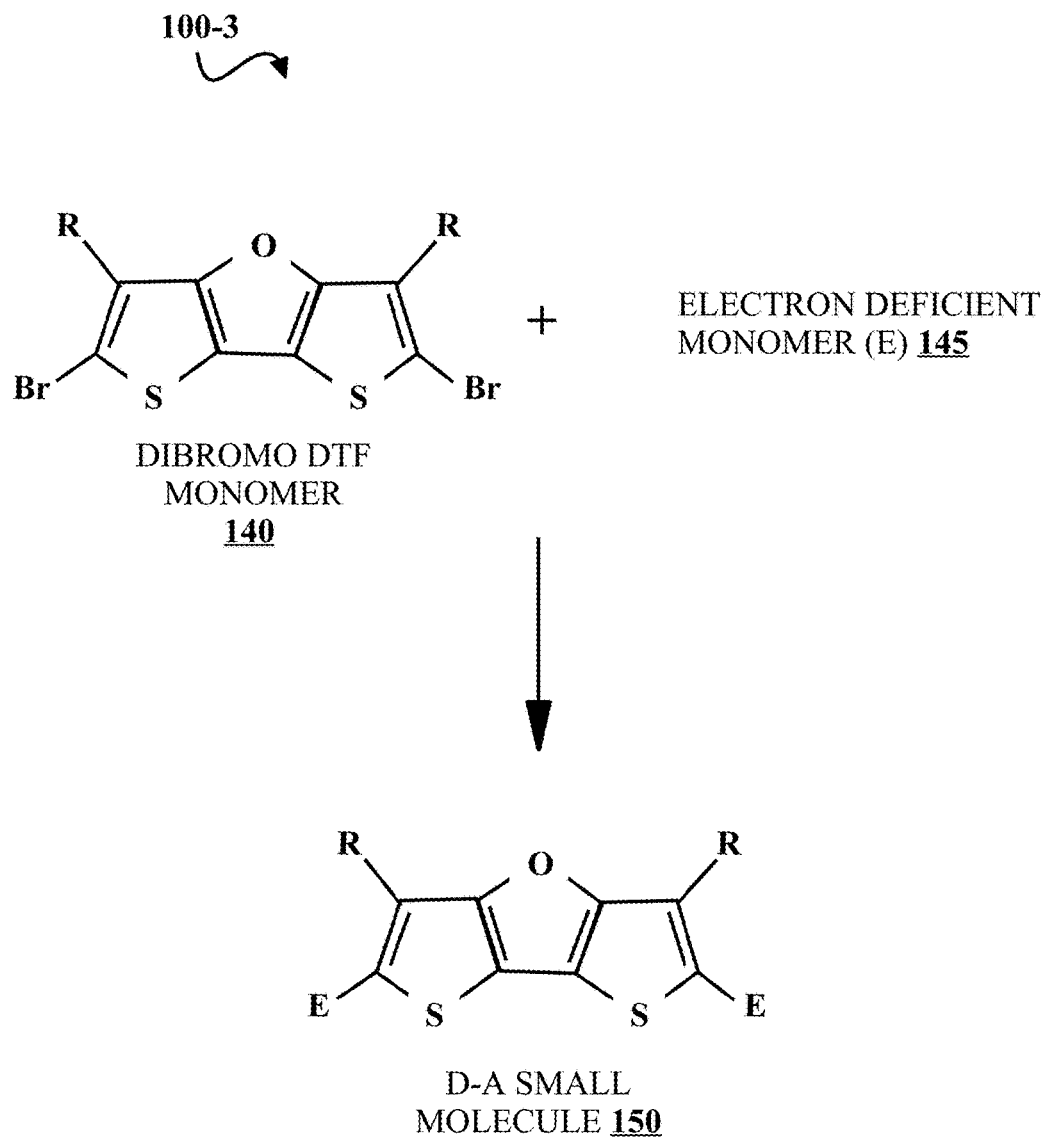
FIG. 1B is a diagrammatic summary of steps in a process of forming an organic semiconducting small molecule, according to some embodiments.
Figure 1C:
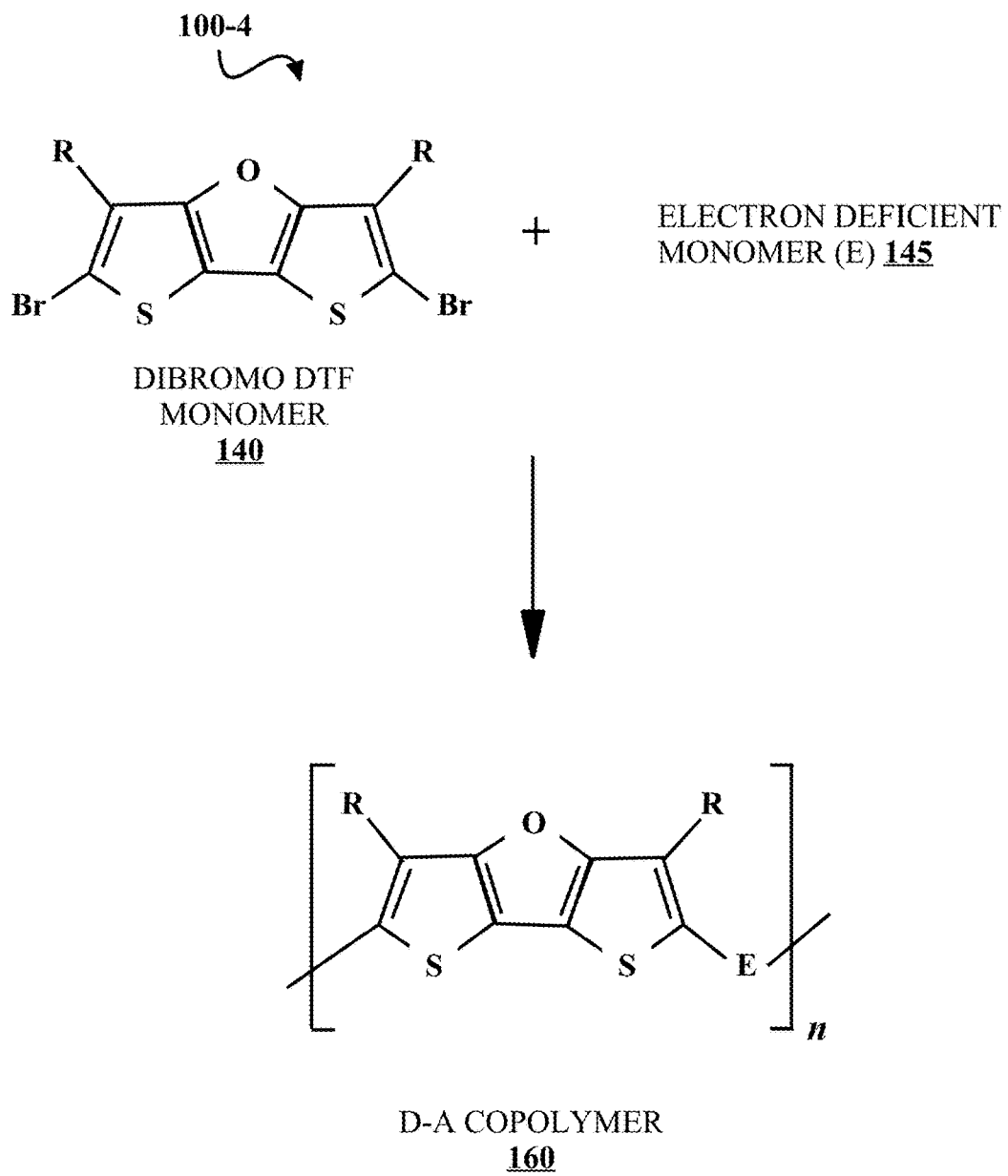
FIG. 1C is a diagrammatic summary of steps in a process of forming an organic semiconducting copolymer, according to some embodiments.

FIGS. 1A, 1B, and 1C summarize steps in the syntheses of compounds discussed herein, according to some embodiments. Examples of these synthetic processes will be discussed in greater detail in FIGS. 2, 4, 5, 6, 8, and 9.

FIG. 1A is a diagrammatic summary of steps in processes 100-1 and 100-2 of forming, respectively, a dibrominated furan compound 130 and a dithienofuran compound 140, according to some embodiments. The first diagram illustrates a process 100-1 of converting furan-2,5-dicarboxylic dimethyl ester (FDME) 110 into a 3,4-dibrominated furan compound 130, according to some embodiments. FDME can come from a bio-renewable precursor before becoming involved in the synthesis of compound 130. The 3,4-dibrominated furan compound 130 can be involved in the synthesis of organic semiconducting compounds discussed herein, according to some embodiments. Details of the synthesis of compound 130 will be discussed in FIG. 2.

Also shown in FIG. 1A is a summary of a process 100-2 of converting the 3,4-dibrominated furan compound 130 into a dibromo dithienofuran (DTF) compound 140, according to some embodiments. The dibromo-DTF monomer 140 and its derivatives can be monomers in semiconducting organic small molecules and copolymers, as discussed below. The dibromo-DTF monomer 140 shown in FIG. 1A has two substituents in addition to its bromo substituents. These are both labeled R, though these substituents do not necessarily need to be identical substituents. R can represent various substituents, including alkanes, alkenes, fluorinated alkanes, ring structures with or without heteroatoms, etc., as will be discussed in greater detail below. Details of the synthesis of the dibromo-DTF monomer 140 will be discussed with respect to FIG. 4.

FIG. 1B is a diagrammatic summary of steps in a process 100-3 of forming an organic semiconducting small molecule 150, according to some embodiments. As indicated here, the dibromo-DTF monomer 140 can be a building block in the synthesis of an organic semiconducting small molecule 150. In some examples, the dibromo-DTF monomer 140 and its derivatives can react with at least one monomer having greater electron affinity. In FIG. 1B, this is referred to as the "electron deficient monomer (E)" 145. Small molecules with monomers of different electron affinities can be called donor-acceptor (D-A) small molecules 150, wherein the "acceptor" monomer has a greater electron affinity than the "donor" monomer and, due to this property, can accept electrons from the more electron rich donor. The exemplary D-A small molecule 150 illustrated here combines one donor monomer, the dibromo-DTF monomer 140, and two equivalents of an acceptor (electron deficient) monomer 145. Details of an example of the synthesis of a D-A small molecule are discussed with regard to FIG. 8.

FIG. 1C is a diagrammatic summary of steps in a process 100-4 of forming an organic semiconducting copolymer 160, according to some embodiments. The dibromo-DTF monomer 140 can be a building block in the synthesis of an organic semiconducting copolymer 160, as it was in the process 100-3 of forming the D-A small molecule 150 in FIG. 1B. In some examples, the dibromo-DTF monomer 140 and its derivatives can react with an electron deficient monomer 145. Polymers with alternating monomers of different electron affinities can be called donor-acceptor (D-A) copolymers 160, wherein the "acceptor" monomer has a greater electron affinity than the "donor" monomer and, due to this property, can accept electrons from the more electron rich donor. The exemplary D-A copolymer 160 shown here comprises repeating units of one donor monomer, the dibromo DTF monomer 140, and one acceptor (electron deficient) monomer 145. Details of an example of the synthesis of a D-A copolymer are discussed with respect to FIG. 9.

It should be understood that the chemical reaction diagrams illustrated herein are prophetic examples and are not limiting; they can vary in reaction conditions, components, methods, etc. The details of synthetic processes described below include reaction conditions (e.g., temperature, time, solvent, identity of inert gases, methods, etc.) and reagents, but these are simply examples and can vary in other embodiments. In addition, reaction conditions can optionally be changed over the course of a process. Further, in some embodiments, processes can be added or omitted while still remaining within the scope of the disclosure, as will be understood by a person of ordinary skill in the art.

Figure 2:
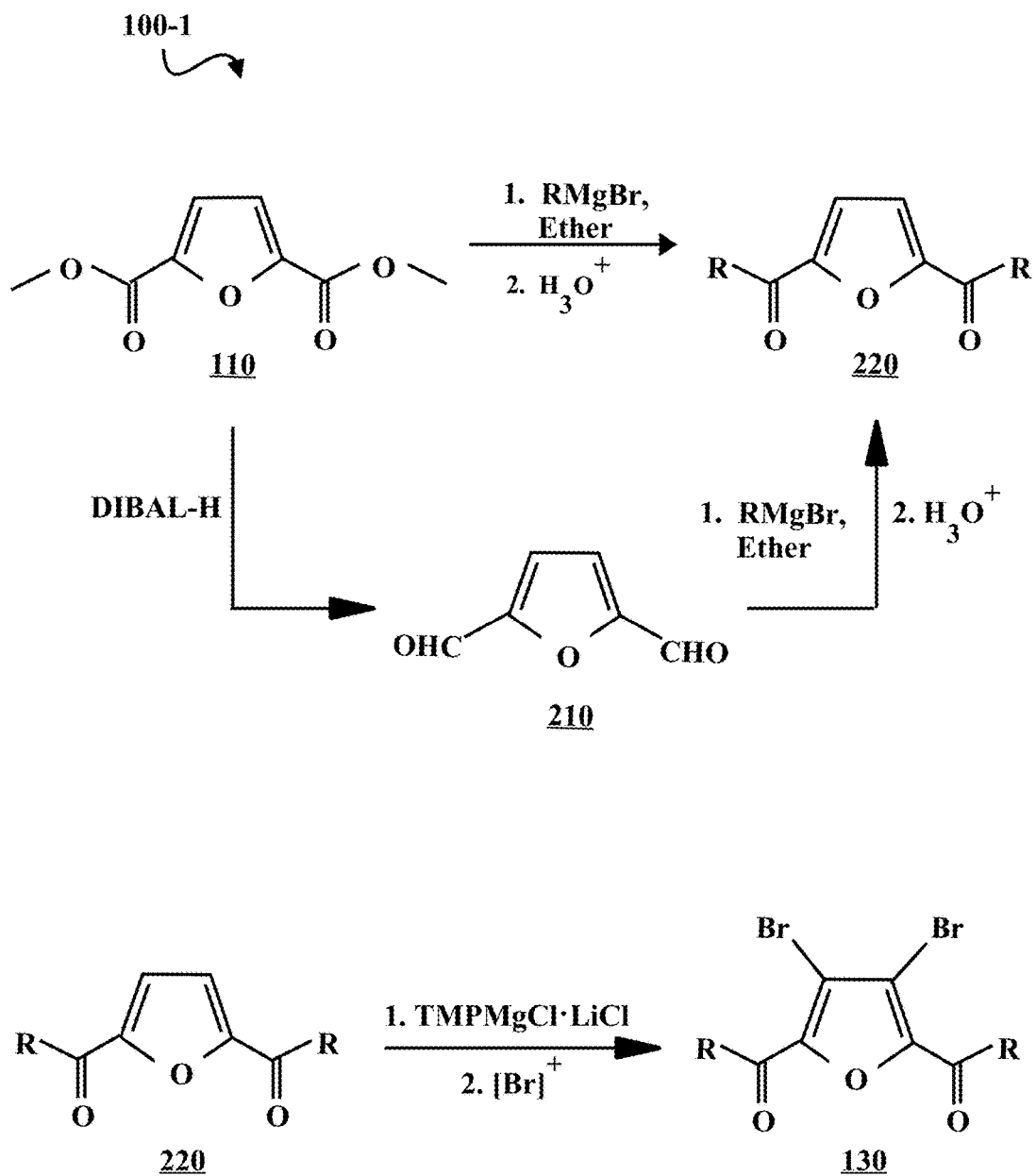
FIG. 2 is a chemical reaction diagram illustrating a process of synthesizing a bis-alkylketone furan and a dibrominated furan compound, according to some embodiments.
Figure 3:
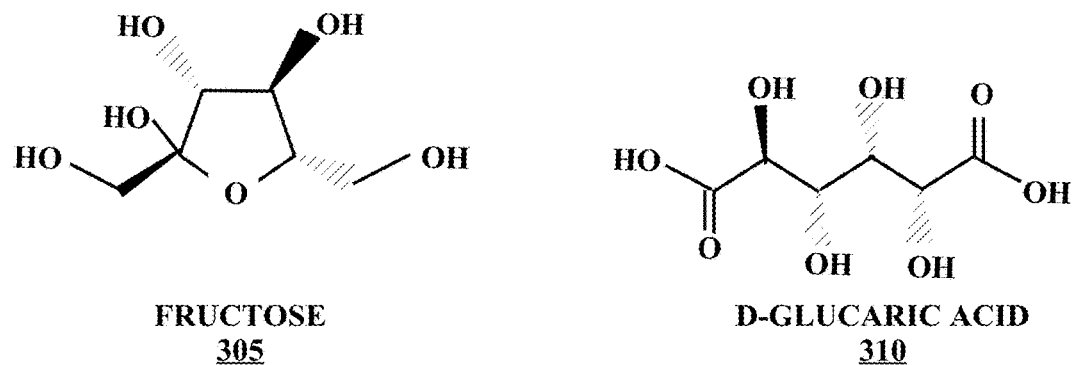
FIG. 3 is a diagrammatic representation of examples of bio-renewable compounds that can be involved in the production of furan-2,5-dicarboxylic dimethyl ester (FDME) according to some embodiments.
Figure 3:
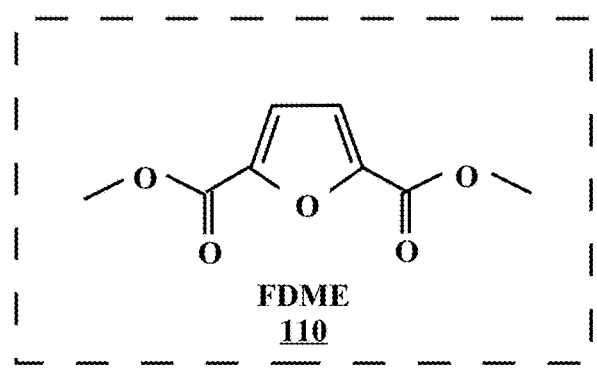
Figure 3:
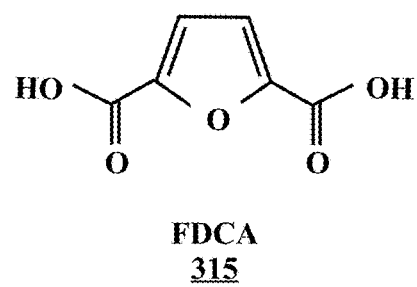

FIG. 2 is a chemical reaction diagram illustrating a process 100-1 of synthesizing a bis-alkylketone furan compound 220 and a 3,4-dibrominated furan compound 130, according to some embodiments. Process 100-1 was introduced in FIG. 1A, and an example of this process is described in greater detail here. FIG. 2 illustrates process 100-1 as broken into two parts. The first part illustrates the conversion of furan-2,5-dicarboxylic dimethyl ester (FDME) 110 to a bis-alkylketone furan compound 220. In some embodiments, FDME 110 can optionally be obtained by synthesis reactions involving bio-renewable compounds, though this is not necessary. Bio-renewable compounds are compounds that can be obtained from renewable sources, such as plant products, animal products, microorganisms, etc. Examples of bio-renewable compounds are illustrated in FIG. 3.

Process 100-1 can begin by converting FDME 110 to a bis-alkylketone furan 220 via a carbon-carbon bond formation reaction, according to some embodiments. In some embodiments, process 100-1 can be accomplished by reacting FDME 110 with a Grignard or lithium reagent. A Grignard reagent comprises an alkyl-, vinyl-, or aryl-magnesium halide. Process 100-1 illustrates the use of a Grignard reagent, RMgBr, where R can be an alkyl group, though the identities of optional R groups will be discussed in greater detail below. Alkyl groups include hydrocarbons having one or more carbon atoms that are connected to one another by single bonds. Grignard reactions can take place in the presence of one or more ethereal solvents, such as tetrahydrofuran (THF), diethyl ether, di-tert-butyl ether, etc. In addition, the Grignard reaction can be quenched by a proton source. Protons are generally written as H$^+$ in chemical reaction diagrams, and when they are in the presence of water (e.g., in an aqueous environment), they are often written as H$^+$/H$_2$O or H$_3$O$^+$. In FIG. 2, the proton source in process 100-1 is denoted H$_3$O$^+$, but this should not be taken to limit the proton source to aqueous environments, or to suggest that the Grignard reaction necessarily takes place in the presence of water.

One example of how the conversion of FDME 110 to a bis-alkylketone furan 220, as illustrated in FIG. 2, can be carried out is by adding a THF solution of an alkylmagnesium bromide, denoted RMgBr in FIG. 2, to a solution of FDME 110. The mixture can then be stirred at low temperature (e.g., −78° C.) before being quenched by a proton source, such as an aqueous solution of HCl. The aqueous layer can then be extracted with an organic solvent, such as diethyl ether. A drying agent, such as magnesium sulfate, can be added to the combined organic phases in order to remove any additional water left in the solution. Following this, the mixture can be concentrated and purified by column chromatography. The purified sample can contain the bis-alkylketone furan 220.

In some cases, over-alkylation of FDME 110 can occur during process 100-1. If this occurs, the FDME can be reduced to a bis-aldehyde furan 210 using a hydrogen atom source. Two examples of hydrogen atom sources that can be used in this reaction are diisobutylaluminium hydride (DIBAL-H) and sodium bis(2-methoxyethoxy)aluminiumhydride (Red-Al), though others can be employed. Compound 210 can then be transformed into compound 220 using any of the possible methods that can be used to convert compound 110 to compound 220. In the exemplary process 100-1 illustrated in FIG. 2, the same conditions are used in both reactions, but this need not be the case. Further, the conversion of compound 210 to compound 220 can optionally be carried out at higher temperatures than the conversion of compound 110 to compound 220. For example, compound 210 can be converted to compound 220 at 0° C.

The process 100-1 illustrated in FIG. 2 can include forming a 3,4-dibrominated bis-alkylketone furan compound 130. In this example, the bis-alkylketone 220 can be converted to a 3,4-dibrominated bis-alkylketone furan 130 by a bromination reaction. This can be accomplished through various methods. One of these, shown in FIG. 2, is the reaction of the bis-alkylketone 220 with a 2,2,6,6-tetramethylpiperidinyl magnesium chloride lithium chloride complex (TMPMgCl.LiCl), followed by the addition of an electrophilic bromine source, generically denoted [Br]+. Electrophilic bromine can come from various sources, including elemental bromine ($Br_2$), N-bromosuccinimide (NBS), benzenesulfonyl bromide, dibromoethane, tetrabromoethane, hexabromoethane, sulfonyl bromides, and others. The addition of $[Br]^+$ can result in the binding of one or more bromine substituents to compound 220, yielding the 3,4-dibrominated bis-alkylketone furan 130.

One example of how the process of forming the 3,4-dibrominated bis-alkylketone furan 130 can be carried out is to add, dropwise and at low temperature (e.g. −78° C.), an anhydrous solution of the bis-alkylketone 220 to a THF solution of TMPMgCl.LiCl. This addition is carried out under an inert gas such as argon or nitrogen. The mixture is then stirred at low temperature for approximately an hour prior to the addition of an electrophilic bromine source. Upon addition of the electrophilic bromine, the mixture is stirred at low temperature for longer than an hour and then allowed to warm to room temperature (i.e., a temperature ranging from 15° C. to 30° C.). Once at room temperature, the reaction is quenched with a saturated aqueous solution of ammonium chloride. The aqueous layer is extracted with an organic solvent, and additional water is removed from the mixture by adding a drying agent, such as magnesium sulfate. The mixture is concentrated and then purified by column chromatography.

FIG. 3 is a diagrammatic representation of examples of bio-renewable compounds that can be involved as precursors in the production of FDME 110, according to some embodiments. One of these is fructose 305, a sugar that can be produced through photosynthesis and is found in many plants. Other examples include aldaric acids, which are polyhydroxy dicarboxylic acids that can be derived from aldoses through oxidation at both terminal carbon atoms. D-Glucaric acid 310 is one example of an aldaric acid, but this is for illustrative purposes, and other aldaric acids can be used. It is possible to derive an aldaric acid from a naturally occurring aldose, though this is not necessary. Another example involves an enzyme, such as oxidoreductase HmfH, that can react with molecular oxygen to produce a precursor for FDME 110, furan-2,5-dicarboxylic acid (FDCA) 315. It should be understood that these bio-renewable substances are only examples, and other compounds can be used in the production of FDME. Further, the compounds discussed here, as well as other compounds involved in the production of FDME, can be obtained from sources that are not bio-renewable. Additionally, FDME can be obtained commercially or through other means.

Figure 4:
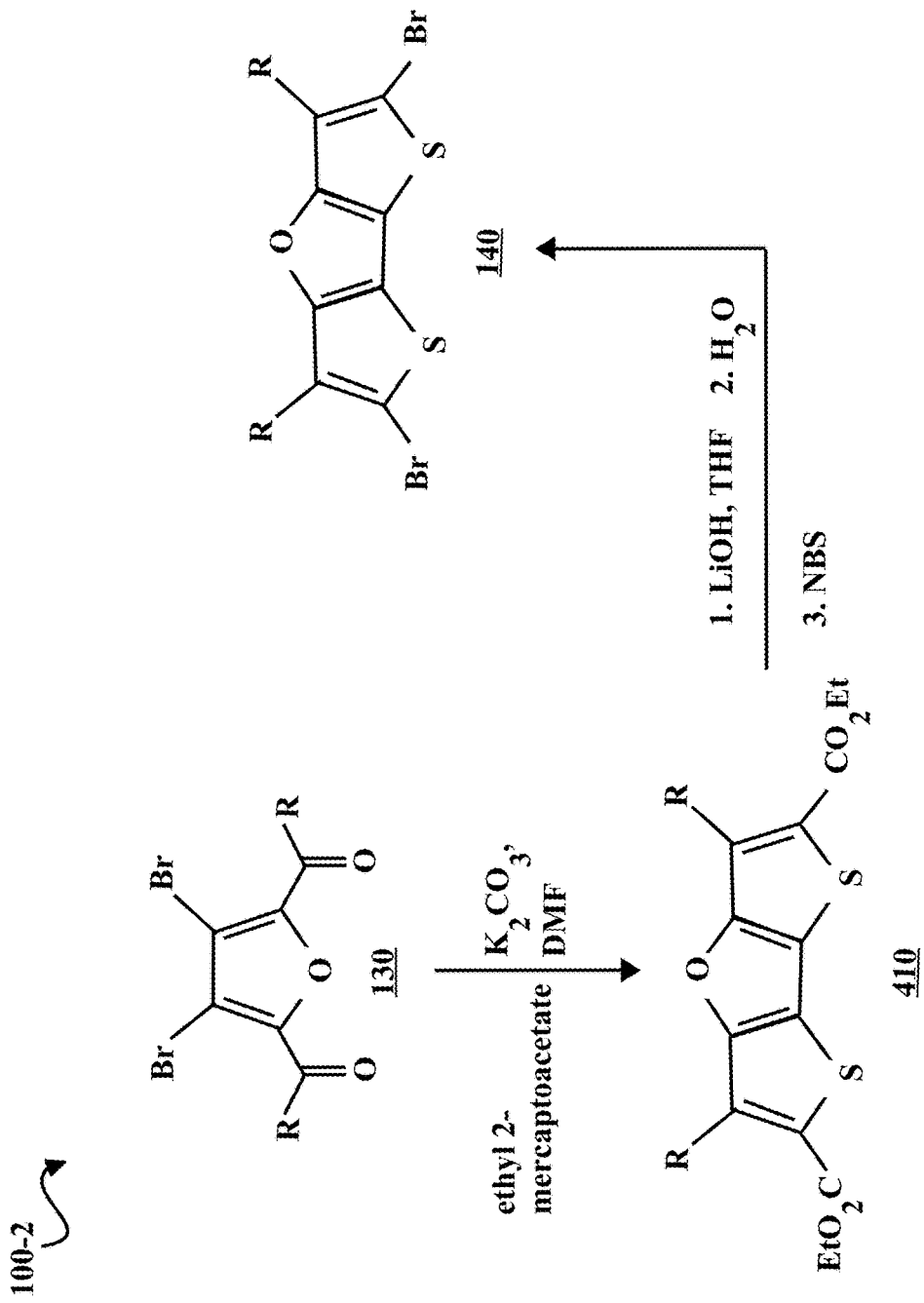
FIG. 4 is a chemical reaction diagram illustrating a process of synthesizing a substituted dibromo dithienofuran compound, according to some embodiments.

FIG. 4 is a chemical reaction diagram illustrating a process 100-2 of synthesizing a substituted dibromo dithienofuran (DTF) compound 140, according to some embodiments. In this example, the dibromo DTF compound 140 has alkyl substituents. Process 100-2 was introduced in FIG. 1A, and an example of this process is described in greater detail here. A first step in process 100-2 yields a bis-alkyl-DTF-diester fused ring structure 410 in a cyclization reaction, and a second step in process 100-2 yields a dibromo bis-alkyl-DTF monomer (a dibromo-DTF compound) 140.

The process 100-2 can involve two steps. In one example of how the first step of process 100-2 can be carried out, the 3,4-dibrominated furan 130 is mixed with potassium carbonate ($K_2CO_3$) in the solvent DMF. To this mixture, ethyl-mercaptoacetate is added dropwise at a temperature warmer than room temperature (e.g., 60° C.). The mixture is stirred for approximately 48 hours under an inert gas, such as nitrogen or argon. The mixture is then poured into water and the organic and aqueous layers are allowed to separate. The aqueous layer is extracted with ethyl acetate, and the organic layer is washed with water and brine (a concentrated aqueous solution of a salt, such as sodium chloride). Water is removed from the organic layers by adding a drying agent, such as magnesium sulfate. The solvent is then evaporated, and the residue purified by column chromatography.

Compound 410 has two ester substituents, and they can be replaced with halogen atoms (e.g., bromine or iodine) during a second step in process 100-2, according to some embodiments. An example of a process of replacing the ester substituents with bromo substituents is illustrated in FIG. 4. In this example, a base (LiOH) is added to a THF solution of the bis-alkyl DTF-diester compound 410. An electrophilic bromine source, such as N-bromosuccinimide (NBS), is then added and the mixture is stirred for approximately 12 hours at room temperature (i.e., 15° C. to 30° C.). In some embodiments N-iodosuccinimide can be used in place of NBS, resulting in iodo substituents in the place of bromo. The mixture is then extracted with an organic solvent, such as dichloromethane. The organic layers are washed with a saturated aqueous solution of sodium bicarbonate, followed by water, and then brine. Water is removed from the organic layers by adding a drying agent, such as magnesium sulfate. The mixture is concentrated and then added to a polar solvent, such as ethanol, in order to form a precipitate. The precipitate is purified by recrystallization. In some embodiments, process 100-2 can result in the formation of an alkylated dibromo-DTF monomer 140, an example of which was introduced in FIG. 1A.

FIG. 4 illustrates one example of a synthesis of the alkylated dibromo-DTF monomer 140 but, in other embodiments, a compound such as this can be obtained through alternate processes. One example of an alternate route to compound 140 can occur via decarboxylation of compound 410 using copper powder in quinoline at a high temperature (e.g., 250° C.), followed by bromination. Further, this process can be carried out under varying reaction conditions or with other reagents.

Figure 5:
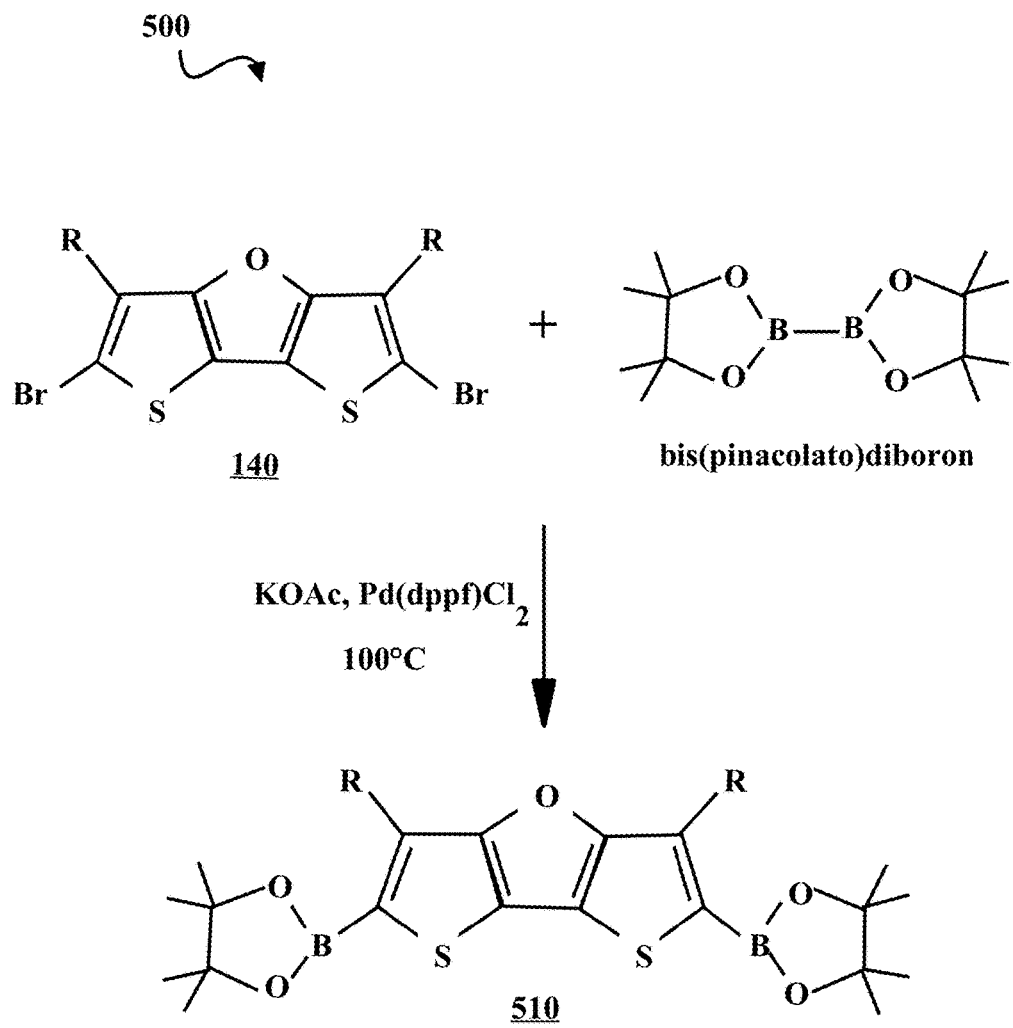
FIG. 5 is a chemical reaction diagram illustrating a process of synthesizing a bis-boronic ester-DTF monomer, according to some embodiments.

FIG. 5 is a chemical reaction diagram illustrating a process 500 of synthesizing a bis-boronic ester-DTF monomer 510, according to some embodiments. This compound is one of several that can be used to synthesize an organic semiconducting D-A small molecule or copolymer. The process 500 of forming the bis-boronic ester-DTF monomer 510 can involve the reaction of an alkylated dibromo-DTF monomer 140 with bis(pinacolato)diboron. In this example, the process 500 is assisted by a palladium catalyst, [1,1'-bis(diphenylphosphino)ferrocene] dichloropalladium], abbreviated $Pd(dppf)Cl_2$, at a high temperature (e.g., 100° C.) in the presence of potassium acetate (KOAc). Other catalysts, reagents, or reaction conditions can be used in some embodiments.

Figure 6:
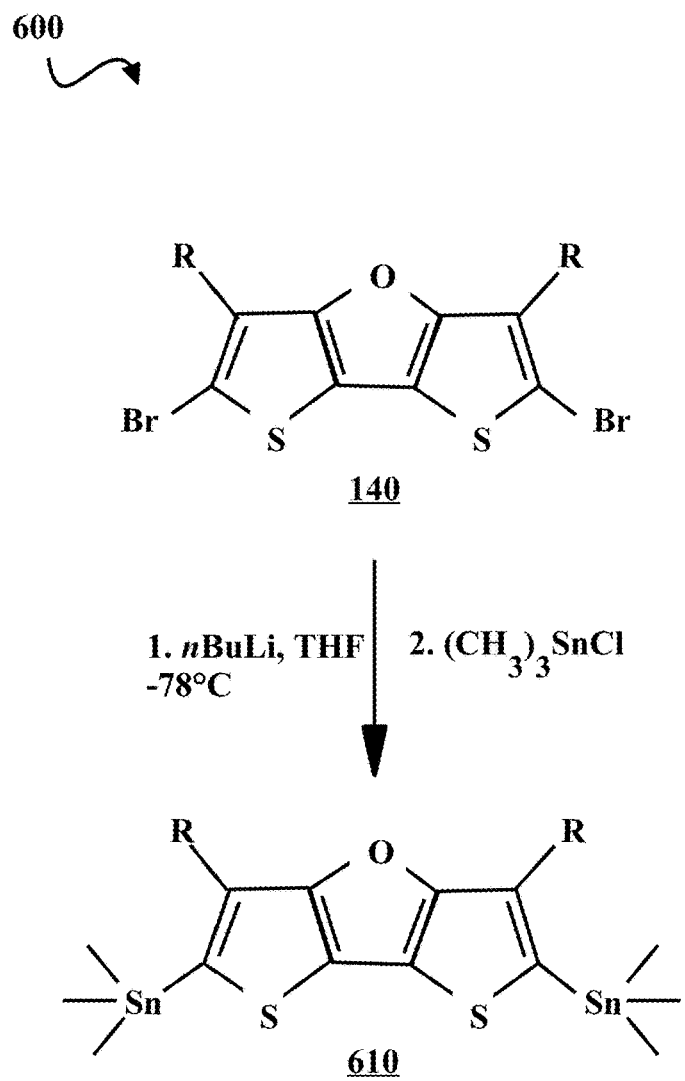
FIG. 6 is a chemical reaction diagram illustrating a process of synthesizing a bis-trialkylstannyl-dithienofuran monomer, according to some embodiments.

FIG. 6 is a chemical reaction diagram illustrating a process 600 of synthesizing a bis-trialkylstannyl-dithienofuran (DTF) monomer 610, according to some embodiments. Like the bis-boronic ester-DTF monomer 510 discussed with respect to FIG. 5, this compound 610 is one of several that can be used to synthesize an organic semiconducting D-A small molecule 150 or copolymer 160. In the exemplary process 600, n-butyllithium is added to the dibromo-DTF monomer 140 at low temperature (e.g., −78° C.) under an inert gas, such as argon or nitrogen. In one approach, the mixture is stirred for longer than one hour at 0° C. A solution of trimethylstannane chloride, $(CH_3)_3SnCl$ is added, and the mixture is allowed to reach room temperature (i.e., 15° C. to 30° C.). The mixture is stirred at room temperature for approximately 12 hours before being combined with water. The organic and aqueous layers are then separated, and the aqueous layer is extracted with an organic solvent. Additional water can be removed from the mixture by adding a drying agent, such as magnesium sulfate. The mixture can be concentrated, and residual $(CH_3)_3SnCl$ can be removed by heating the mixture under reduced pressure (e.g., under vacuum). Process 600 can take place in various solvents, such as ethers and THF. Other catalysts, reagents, or reaction conditions can be used in some embodiments.

Figure 7:
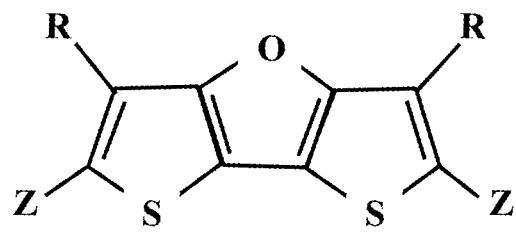
FIG. 7 is a diagrammatic representation of a dithienofuran (DTF) core monomer and three of its optional substituents, according to some embodiments.

FIG. 7 is a diagrammatic representation of a dithienofuran (DTF) monomer 710 and three of its optional substituents, according to some embodiments. The DTF monomer 710 forms the core of the DTF monomers disclosed herein. The DTF core monomer 710 illustrated here has four substituents, two labeled "Z" and two labeled "R." Examples of possible R substituents can include hydrogen atoms, alkanes, alkenes, fluorinated alkanes, etc. The Z substituents can vary and the examples shown in FIG. 7 correspond to the substituted DTF monomers 140, 510, and 610, the syntheses of which were described with respect to FIGS. 4, 5, and 6, respectively. In some embodiments, a DTF monomer can have non-identical R or Z groups (e.g., a monomer can have two different alkyl R substituents).

There are many examples of R groups that can be substituents on the DTF core monomer 710. One possible class of R group substituents is hydrocarbons. Hydrocarbons can be saturated or unsaturated. A saturated hydrocarbon can be an alkyl group. Alkyl groups can include straight-chain, branched, and cyclic alkanes. Alkanes can include any hydrocarbon having one or more carbon atoms, wherein the carbon atoms are connected to one another by single bonds and, in most cases, are bound to one or more hydrogen atoms. Cyclic alkanes are those that include one or more rings, which can have three or more carbon atoms. Some examples of R groups can include, but are not limited to, $C_1$-$C_{20}$ linear alkyl chains, $C_2$-$C_{24}$ branched alkyl chains, monoalkyl amines comprised of $C_2$-$C_{20}$ linear alkyl chains or $C_1$-$C_{24}$ branched alkyl chains, dialkylamines comprised of $C_1$-$C_{20}$ linear alkyl chains, $C_1$-$C_{24}$ branched alkyl chains, etc. Alkyls can also be perfluorinated, wherein hydrogen atoms are replaced with fluorine atoms.

The Z substituents in FIG. 7 are those found on the exemplary DTF monomers 140, 510, and 610. As discussed above, compound 140 is a dibromo-DTF monomer, where Z is a bromo substituent; compound 510 is a bis(boronic ester)-DTF monomer, where Z is a boronic ester substituent; and compound 610, is a bis(trimethylstannyl)-DTF monomer, where Z is a trimethylstannyl substituent. Z can also be a number of other substituents, and their identity can be chosen based on how easily they can be cross-coupled to electron deficient monomers during polymerization reactions and reactions to form small molecules.

Figure 8:
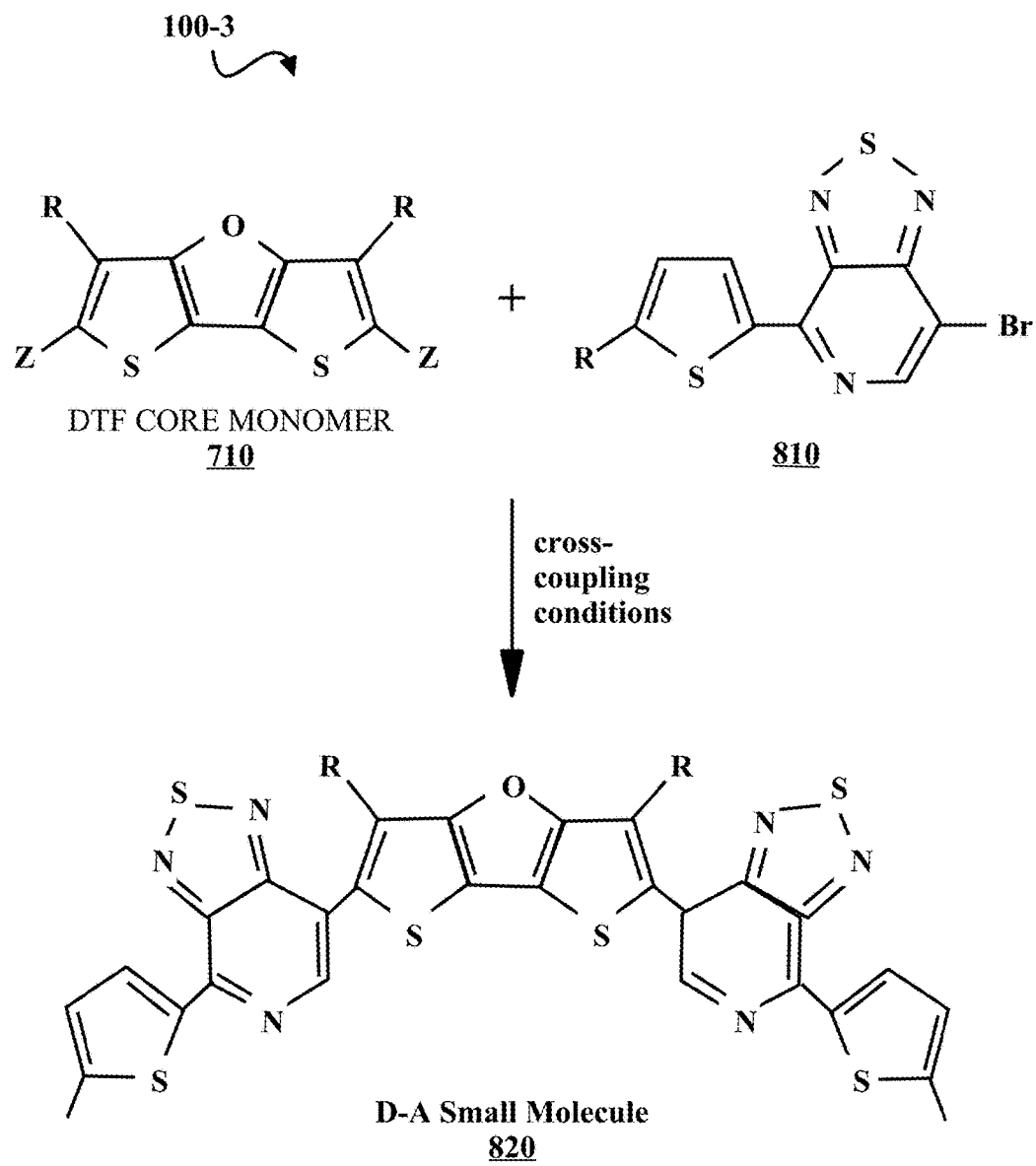
FIG. 8 is a chemical reaction diagram illustrating a process of synthesizing a donor-acceptor small molecule, according to some embodiments.
Figure 9:
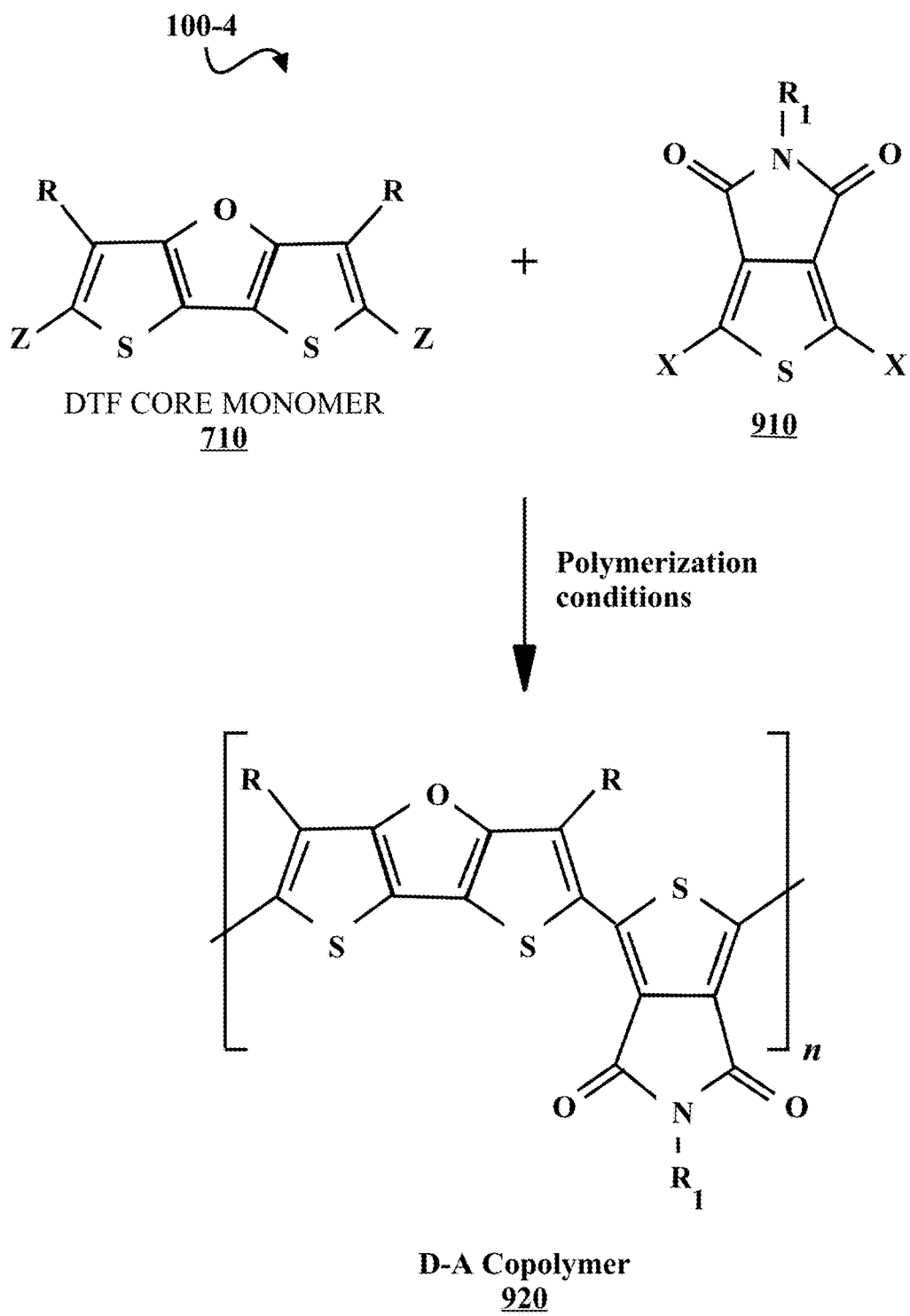
FIG. 9 is a chemical reaction diagram illustrating a process of synthesizing a donor-acceptor copolymer, according to some embodiments.

Each of the compounds illustrated in FIG. 7 is a prophetic example of a monomer that can be used in the processes of forming organic semiconducting electron donor-acceptor (D-A) small molecules 820 and copolymers 920 illustrated in FIGS. 8 and 9. An electron D-A compound is one that has regions of varying electron affinities. A region with greater electron affinity is known as an "acceptor" because it is more likely to accept an electron. Molecules or regions that act as electron acceptors are also known as "electron deficient."

FIG. 8 is a chemical reaction diagram illustrating a process 100-3, which was introduced in FIG. 1B, of synthesizing a donor-acceptor (D-A) small molecule 820, according to some embodiments. This D-A small molecule 820 can act as an organic semiconductor. The example of process 100-3 illustrated in FIG. 8 involves a reaction between a DTF core monomer 710 (e.g., compound 140, 510, or 610) and an electron deficient monomer. There are many types of electron deficient monomers that can be used; a prophetic example of one of these is from a class of molecules known as bromoalkylthienyl-pyridylthiazoles 810, as is shown in FIG. 8. The R substituent on compound 810 can be one of a large variety of substituents, including those listed as possible R substituents on the DTF core monomer 710. Other examples of electron deficient monomers that can be used are discussed with respect to FIG. 7. Examples of reactions that can be conducted to produce the D-A small molecule 820 include a Suzuki reaction, C—H activation, a Stille reaction, etc.

FIG. 9 is a chemical reaction diagram illustrating process 100-4, which was introduced in FIG. 1C, of synthesizing a donor-acceptor (D-A) copolymer 920, according to some embodiments. This D-A copolymer 920 can act as an organic semiconductor. The example of process 100-4 illustrated in FIG. 9 involves forming a D-A copolymer 920 from the reaction between a variably substituted, electron rich DTF core monomer 710 (e.g., 140, 510, and 610) and an electron deficient aromatic monomer. In this example, a DTF monomer 710 reacts with an electron deficient aromatic monomer, a thienopyrrolodione (TPD) compound 910. The R substituent on compound 810 can one of a large variety of substituents, including those listed as possible R substituents on the DTF core monomer 710. Other electron deficient monomers can be used, including those discussed with regard to FIG. 7. These electron deficient monomers can be dibromo functionalized or bis-H functionalized. Process 100-4 can produce a D-A copolymer 920 comprising repeating units of the combined DTF core monomer 710 and electron-deficient monomer, TPD 910. Examples of reactions that can carry out the polymerization in some embodiments can include Suzuki cross-coupling polymerization, Stille cross-coupling polymerization, C—H activation coupling polymerization, etc.

It should be understood that, in some embodiments, the compounds described herein can contain one or more chiral centers. These can include racemic mixtures, diastereomers, enantiomers, and mixtures containing one or more stereoisomer. It should be noted that the disclosed can encompass racemic forms of the compounds as well as individual stereoisomers, as well as mixtures containing any of these.

Figure 10:
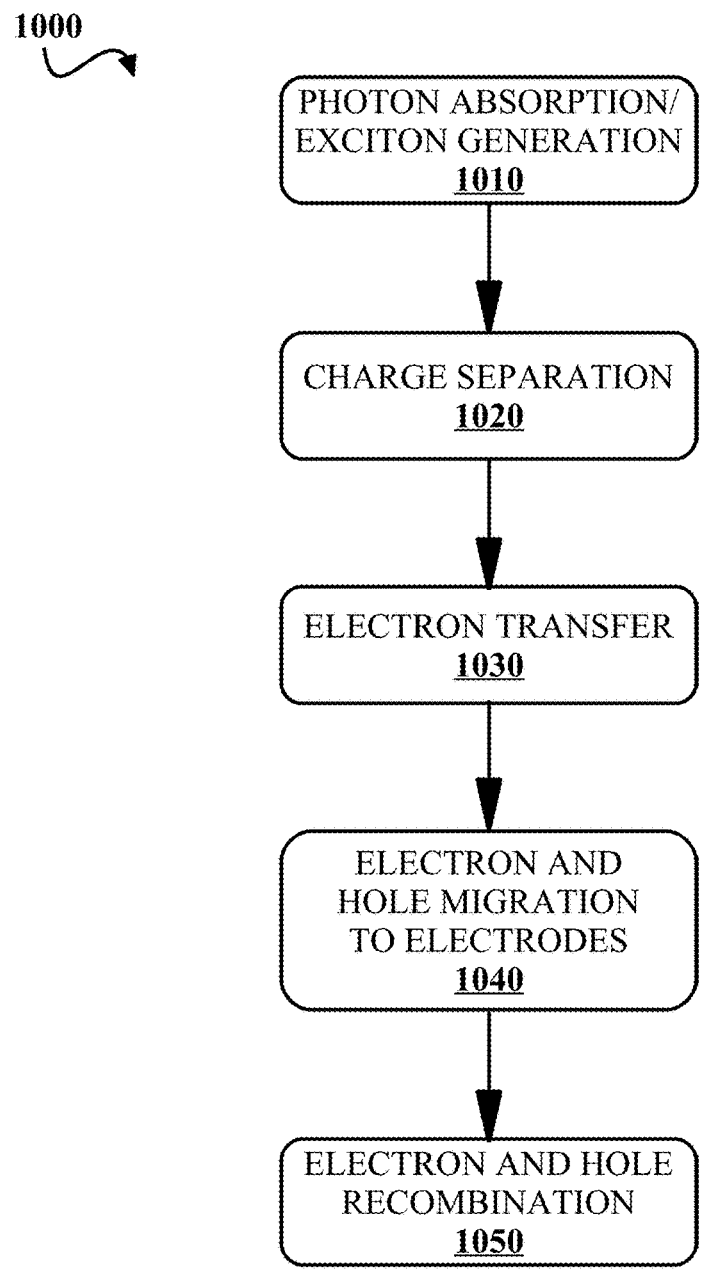
FIG. 10 is a flow diagram illustrating a process of electron excitation and transfer triggered by photon absorption by an organic semiconductor, according to some embodiments.
Figure 11A:
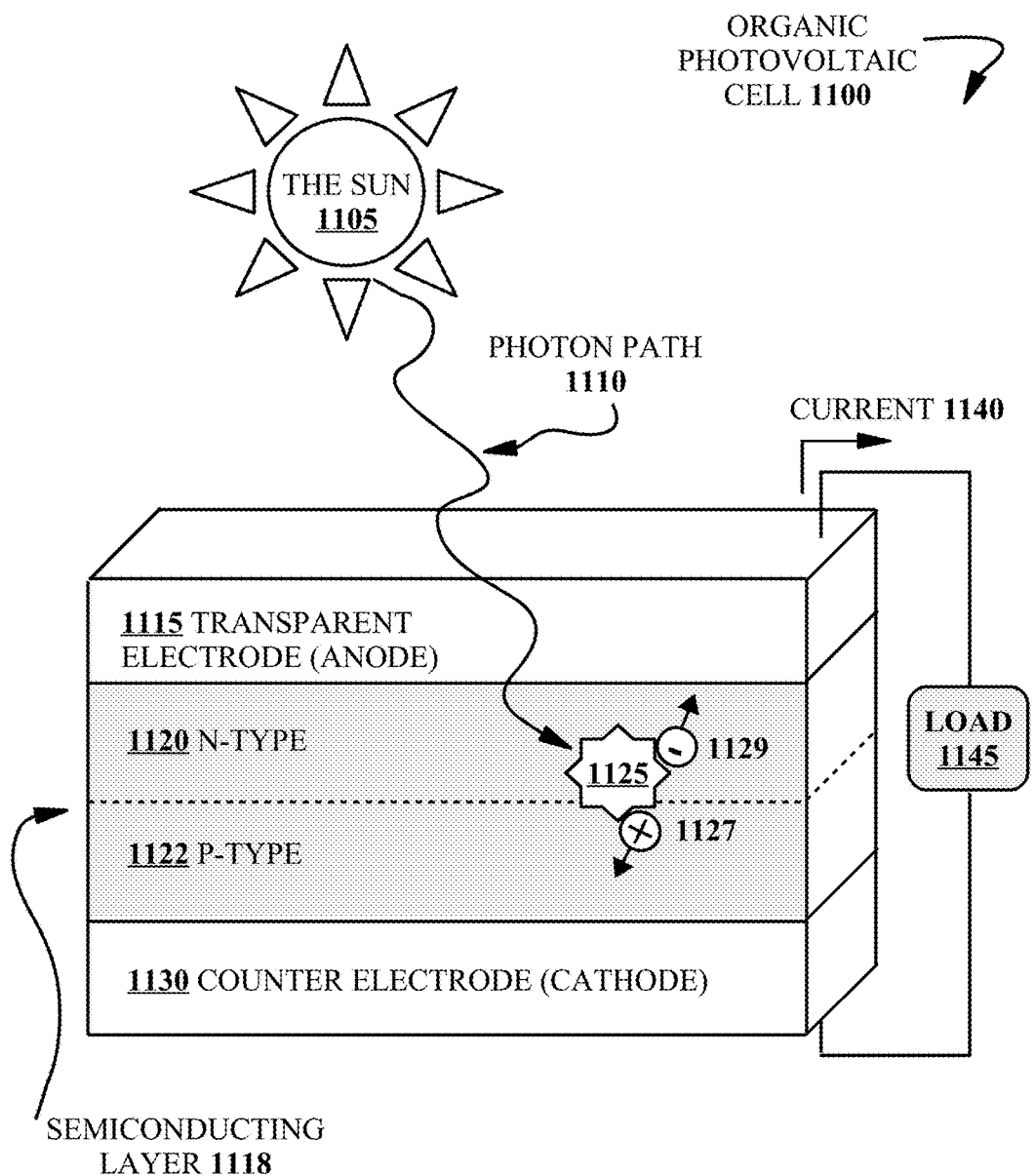
FIG. 11A is a diagrammatic illustration of an exemplary organic photovoltaic (OPV) cell, according to some embodiments.
Figure 11B:
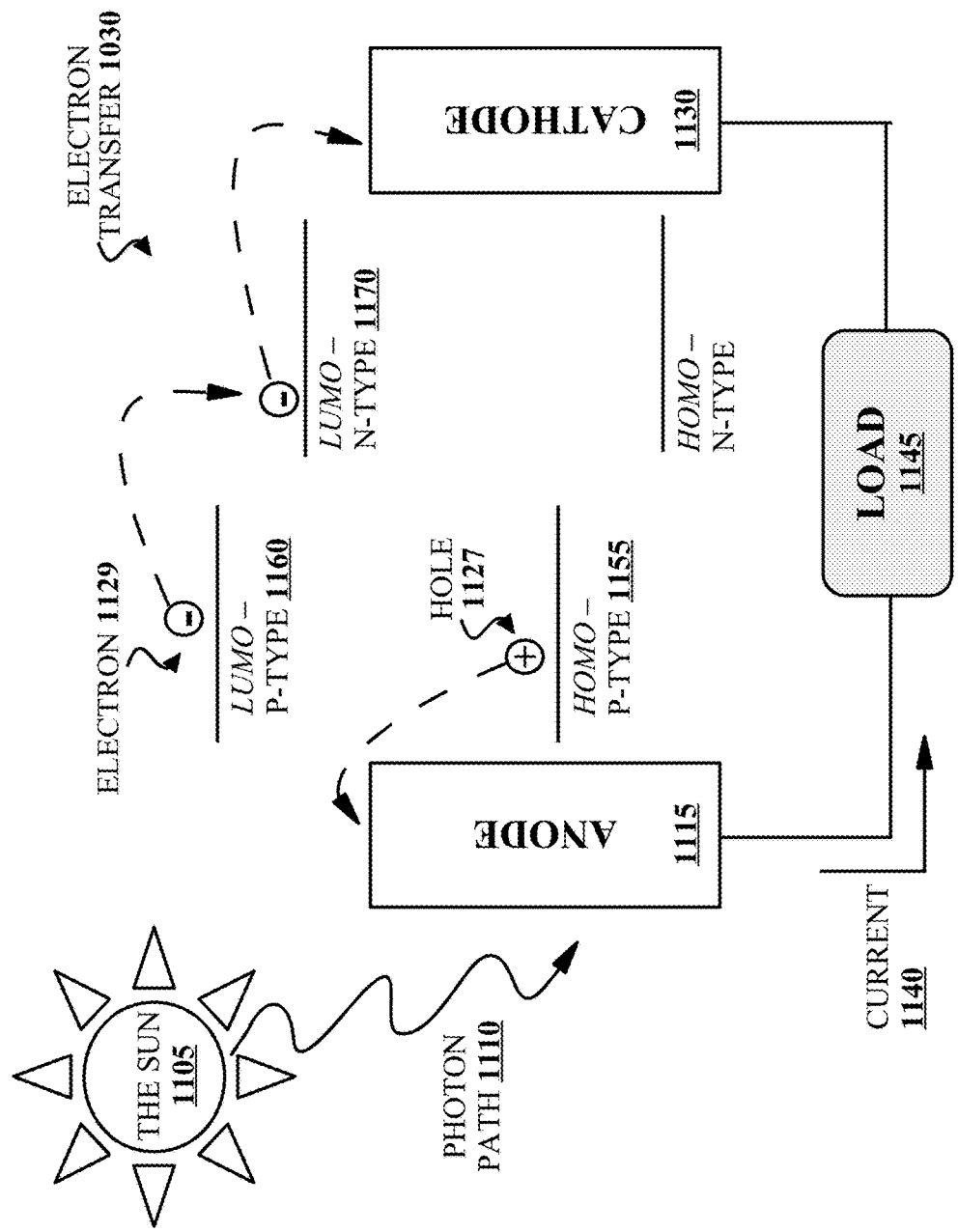
FIG. 11B is a diagram illustrating a process of electron transfer in an organic semiconductor, according to some embodiments.

The D-A small molecules 150 and copolymers 160 described herein can act as organic semiconductors. Organic semiconductors have numerous applications and can be used in many of the same applications as inorganic semiconductors. These applications can include semiconductor devices, such as photovoltaic cells (e.g., solar cells), field effect transistors, light sensors, etc. FIGS. 10, 11A, and 11B illustrate properties and applications of organic semiconducting small molecules and copolymers, such as the ones described herein, in a photovoltaic device, according to some embodiments. These figures will be discussed together.

FIG. 10 is a flow diagram illustrating a process 1000 of electron excitation and transfer in an organic semiconductor (e.g., D-A small molecule 820 or D-A copolymer 920), triggered by photon absorption, according to some embodiments. In this process 1000, energy from light can be converted into electricity. In some examples, process 1000 can take place in an organic photovoltaic (OPV) device or cell, such as cell 1100 in FIG. 11A.

FIG. 11A is a diagrammatic representation of an exemplary organic photovoltaic (OPV) cell 1100, according to some embodiments. An OPV cell 1100 can contain one or more types of semiconducting material, which can be D-A small molecules 150 or D-A copolymers 160. Referring to operation 1010 in FIG. 10, these organic semiconducting materials can absorb at least one photon. An example of photon absorption 1010 by an organic semiconductor in an OPV cell 1100 is illustrated in FIG. 11A. In this example, photons come directly from the sun 1105, though other photon sources can be used (e.g., an ultraviolet (UV) lamp). At least one photon can travel a path 1110 that arrives at the OPV cell 1100. The photon can pass through a transparent electrode 1115 in the OPV cell 1100. In this example, the transparent electrode 1115 is an anode.

The exemplary OPV cell 1100 also includes a semiconducting layer 1118 between two electrodes, 1115 and 1130. This layer can contain organic materials such as the D-A small molecule 820 or the D-A copolymer 920 described with respect to FIGS. 8 and 9. In the semiconducting layer 1118, there can be at least two regions with different electron affinities. As in the case of inorganic semiconductors, such as silicon, organic semiconductors can have n-type 1120 and p-type 1122 regions. An n-type semiconductor is more negatively charged than a p-type semiconductor because it has an excess of electrons, while a p-type semiconductor has an excess of positive charges, known as "holes." In some embodiments, the n-type material 1120 can comprise a D-A small molecule 150 or D-A copolymer 160.

There are a variety of p-type materials 1122 that can be used in the semiconducting layer 1118 of the OPV cell 1100. Some of these include polymers, polymer blends, etc. Some examples of p-type polymers are Poly[2-methoxy-5-(2-ethylhexyloxy)-1,4-phenylenevinylene], commonly abbreviated MEH-PPV; Poly(9,9-dioctylfluorene-alt-benzothiadiazole), commonly abbreviated F8BT; and poly(3-dodecylthiophene-2,5-diyl) regiorandom, commonly abbreviated P3DDT.

The type of semiconducting layer 1118 illustrated in FIG. 11A is known as a bilayer, its two layers being n-type 1120 and p-type 1122 semiconductors. There are other types of semiconducting layers that incorporate n-type 1120 and p-type 1122 semiconducting materials, such as single-layers, bulk heterojunctions, discrete heterojunctions, graded heterojunctions, etc., and the bilayer shown in FIG. 11A should not be taken as limiting.

In FIG. 10, operation 1010, in addition to encompassing photon absorption, can involve the generation of what is known as an "exciton." A photon absorbed by an organic semiconducting material can provide enough energy to excite an electron in the semiconducting layer 1118 of the OPV cell 1100 to a higher energy level. When an electron transitions to a higher energy level, it can be thought of as having left behind a positive charge, known as a "hole." This electron-hole pair is called an exciton. An example of an exciton 1125 is illustrated in FIG. 11A within the semiconducting layer 1118 of the OPV cell 1100.

FIG. 10 also illustrates a charge separation step 1020, wherein the exciton 1125 separates into an electron 1129 and hole 1127 (or negative and positive charges, respectively). In the example illustrated in FIG. 11A, an exciton 1125 is generated in the semiconducting layer 1118, separating into a hole 1127 and an electron 1129. When the exciton 1125 is at an interface between n-type 1120 and p-type 1122 semiconductors, the electron 1129 can travel through the n-type semiconductor and the hole 1127 can travel through the p-type semiconducting region.

In the electron transfer operation 1030 of FIG. 10, when the electron 1129 leaves behind a positively charged hole 1127, which flows through the p-type layer 1120. Operation 1030 will be discussed in greater detail with respect to FIG. 11B. FIG. 10 also illustrates an electron 1129 and hole 1127 migration step 1040. In this step 1040, the electron 1129 in the n-type semiconducting layer 1120 can migrate toward the anode 1115, and the hole 1127 left behind by the transferred electron 1129 can migrate toward the cathode 1130. In the OPV cell 1100 illustrated in FIG. 11A, the cathode is the counter electrode 1130, and the anode is the transparent electrode 1115.

Continuing the description of process 1000, illustrated in FIG. 10, electrons 1129 and holes 1127 that have reached the electrodes in operation 1040 can exit the OPV cell 1100 in operation 1050. After exiting through their respective electrodes, electrons 1029 and holes 1127 can travel through external wires in order to recombine. As seen in FIG. 11A, the flow of electrons begun in operation 1050 can allow a current 1140 to flow through the circuit, which can provide the energy to power some external load 1145. FIG. 11B illustrates the electron transfer 1030 of process 1000 and is discussed in greater detail below.

FIG. 11B is a diagrammatic illustration of a process of electron transfer 1030 in an organic semiconductor, according to some embodiments. It is well known that many metals can conduct electricity (i.e., transfer electrons), and this is why, historically, metal wires (e.g., copper and aluminum wires) have been used in electrical applications. Conductive metals are able to conduct electricity because their electrons are delocalized and can thus move freely and easily though the metal. Other types of inorganic materials, including metalloids (e.g., silicon), have a certain degree of electron delocalization, allowing them to act as semiconductors. Organic materials that can conduct electricity, including organic semiconductors, also rely on electron delocalization. In an organic material, electron delocalization is most easily achieved in what is known as a "conjugated system." Conjugated systems include organic materials with overlapping molecular orbitals in molecules that have alternating single and double or triple bonds. In a conjugated system, electrons in these molecular orbitals are not localized to a particular bond or atom, but can instead move freely through the overlapping orbitals.

Molecular orbitals can have different energy levels. Some molecular orbitals are occupied by electrons, which fill the orbitals with lower energy levels before those with higher energy levels. The highest energy orbital that contains an electron is called the highest occupied molecular orbital (HOMO), and the lowest energy orbital that doesn't contain an electron is called the lowest unoccupied molecular orbital (LUMO). Because electrons fill orbitals beginning with the lowest energy levels, the LUMO is at the next highest energy level after the HOMO. The energy for electron excitation in a conjugated organic system can be provided by a photon, allowing the excited electron to transition from the HOMO to the LUMO. Overlapping LUMOs in a conjugated organic semiconducting material can be thought of as a "conduction band," wherein electrons that are excited into the LUMO become delocalized and can move freely through all overlapping molecular orbitals. This allows the conjugated organic material to conduct electrons in a manner similar to metals and metalloids.

Turning to FIG. 11B, molecular orbitals in an organic semiconducting material are illustrated as being at different energy levels. The HOMOs are the lowest energy levels shown, and the LUMOs are the highest energy levels shown. In this example, the electron 1129 has been excited by a photon 1110 from the sun 1105. Upon excitation, the electron moves from the HOMO of the p-type semiconductor 1155 to the LUMO of the p-type semiconductor 1160, leaving a hole 1127 behind in the p-type HOMO 1155. The electron 1129 is then transferred from the LUMO of the p-type semiconductor 1160 to the LUMO of the n-type semiconductor 1170 in an electron transfer step 1030. The hole 1127 then migrates toward the anode 1115 and can leave the cell through this electrode 1115. In addition, the transferred electron 1129 can leave the cell through the cathode 1130. The electron 1129 and hole 1127 can then travel through an external wire, producing a current 1140 that can power an external load 1145.

An organic photovoltaic (OPV) cell, such as the cell 1100 illustrated in FIG. 11A, can incorporate various components and materials in addition to the type semiconducting organic materials discussed herein. Some examples of these components and materials from which they can be made are discussed below.

In some embodiments, an OPV cell 1100 has two electrodes. A first electrode, e.g., the transparent electrode 1115 in FIG. 11A, can be made of a material with qualities that include, but are not limited to, transparency and conductivity. Some examples of these materials can include metal oxides such as zinc oxides, tin oxides, indium oxides, indium tin oxides, and indium zinc oxides. Additionally, the transparent conducting material can comprise a combination of two or more of these metal oxides. Other combinations can be of two or more metals and metal oxides, such as ZnO:Al or $SnO_2$:Sb. Still other examples can include metals such as vanadium, chromium, copper, zinc, gold, or an alloy thereof. Conductive polymers, such as poly(3-methylthiphene), poly[3,4-(ethylene-1,2-di-oxy)thiophene] (PEDOT), polypyrrole, and polyaniline, are among others can be used. The electrode 1115 can optionally be a flexible electrode made of one or more materials that can include, but are not limited to, Ag nanowires, Cu nanowires, graphene, carbon nanotubes, polymers, and polymer-metal hybrids.

An OPV cell 1100 also contains a second electrode, e.g., the counter electrode, or cathode 1130, shown in FIG. 11A. In some embodiments, this electrode 1130 can be a metal having a small work function. Examples of metals such as this include lithium, sodium, potassium, magnesium, calcium, titanium, indium, yttrium, gadolinium, aluminum, silver, tin, and lead. The metal can also be an alloy. In some embodiments, the counter electrode 1130 can have a multilayered structure. Examples of multilayered structures that can be utilized include LiF/Al, $LiO_2$/Al, LiF/Fe, Al:Li, Al:$BaF_2$, and Al:$BaF_2$:Ba. The second electrode 1130 can also be made of non-metal or metal-non-metal hybrid materials. Examples of these include carbon-sulfur nanotubes, nanofibers, and organic polymers.

As discussed above, an OPV cell 1100 can contain at least one semiconducting organic material in its semiconductor layer 1118. These materials can include some that were not discussed above. A semiconducting organic material can be a conjugated organic molecular compound or compounds, according to some embodiments. Molecules in an OPV cell 1100 can have any level of size or complexity, encompassing monomers, dimers, trimers, polymers, copolymers, and others. They can be combined with one or more materials that may or may not be conductive and may or may not be molecular. Some examples of other conductive materials that can optionally be incorporated are electrolytes, inorganic or ionic substances, metals, some allotropes of carbon, and organic or organometallic substances.

Organic photovoltaic compounds such as those described herein can have a number of applications. For instance, an organic semiconducting D-A small molecule 150 or copolymer 160 can be utilized in flexible OPV cells. Here, the semiconducting compounds can be deposited onto a flexible substrate, examples of which include paper, fabrics, and synthetic polymers, such as polyethylene terephthalate (PET). Flexible OPV cells can be incorporated into items such as clothing, flexible electronic screens, etc.

The examples discussed herein and represented in the accompanying drawings may make reference to particular details. However, it will be understood that there are various modifications that can be made while retaining the spirit and scope of the disclosure. These would be easily recognized and carried out by one of ordinary skill in the art.

What is claimed is:

1. A device comprising:
a first electrode;
a second electrode; and
semiconducting layer disposed between the first electrode and the second electrode and including a photoactive layer, wherein the photoactive layer includes a semiconducting compound of the formula:

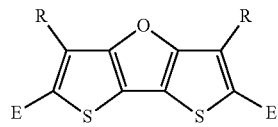

wherein each of R is selected from a group consisting of a $C_1$-$C_{20}$ linear alkyl chain, a $C_2$-$C_{24}$ branched alkyl chain, and a hydrogen atom; and
wherein each of E is an electron deficient substituent selected from a group consisting of a bromoalkylthienyl-pyridylthiazole, a benzodithiazole, a pyridyldithiazole, a diketopyrrolopyrrole, a thienopyrrolodione, a thienothiophene ester, a fluorinated thienothiophene ester, a dithienotetrazine, a thienoquinoxaline, a benzoquinoxaline, and a pyridylquinoxaline.

2. The device of claim 1, wherein the first electrode and the second electrode comprise at least one material selected from a group consisting of a metal, a metal oxide, a metal alloy, a conductive polymer, Ag nanowires, Cu nanowires, graphene, carbon nanotubes, a polymer-metal hybrid, carbon-sulfur nanotubes, nanofibers, and an organic polymer.

3. The device of claim 1, wherein the semiconducting layer is a bilayer.

4. The device of claim 1, wherein the semiconducting layer is a bulk heterojunction.

5. The device of claim 1, wherein the semiconducting layer further comprises a semiconducting material selected from a group consisting of fullerenes, a polymer, and a polymer blend.

6. The device of claim 1, wherein the semiconducting compound is synthesized in a reaction between a dithienofuran core monomer and the electron deficient monomer.

7. The device of claim 1, wherein the device is an organic photovoltaic cell.

8. The device of claim 1, wherein the device is a field effect transistor.

9. The device of claim 1, wherein the device is a flexible organic photovoltaic cell.

10. The device of claim 1, wherein the device is a light sensor.

* * * * *